United States Patent [19]
Keene

[11] Patent Number: 4,543,096
[45] Date of Patent: Sep. 24, 1985

[54] EYEDROP DISPENSER WITH EYELID OPENING MEANS

[76] Inventor: Thomas Keene, 615 N. 57th St., Philadelphia, Pa. 19131

[21] Appl. No.: 520,651

[22] Filed: Aug. 5, 1983

[51] Int. Cl.$^4$ .............................................. A61M 7/00
[52] U.S. Cl. .................................... 604/300; 604/214
[58] Field of Search ........................ 604/214, 294–302

[56] References Cited

U.S. PATENT DOCUMENTS

| | | | |
|---|---|---|---|
| 1,023,042 | 4/1912 | Scott | 604/214 X |
| 4,085,750 | 4/1978 | Bosshold | 604/302 |
| 4,131,115 | 12/1978 | Peng | 604/297 |
| 4,386,608 | 6/1983 | Ehrlich | 604/298 |

FOREIGN PATENT DOCUMENTS

| | | | |
|---|---|---|---|
| 594860 | 3/1934 | Fed. Rep. of Germany | 604/302 |
| 1025304 | 4/1953 | France | 604/302 |

*Primary Examiner*—Dalton L. Truluck
*Attorney, Agent, or Firm*—Steele, Gould & Fried

[57] ABSTRACT

An eyedrop dispenser is disclosed which includes a plastic squeeze bottle having a dispensing nozzle at one end. A collar overfits the dispenser end of the bottle and carries a pair of cooperating, forwardly extending fingers for eyelid contacting purposes. The fingers terminate forwardly in respective eyelid contactors and one finger is pivotally movable relative to the other to spread the eyelid contactors during the eyedrop dispensing process. The movable finger includes an operator extension which engages the bottle sidewall when the eyelid contactors are separated to squeeze the bottle and dispense the eyedrops.

3 Claims, 5 Drawing Figures

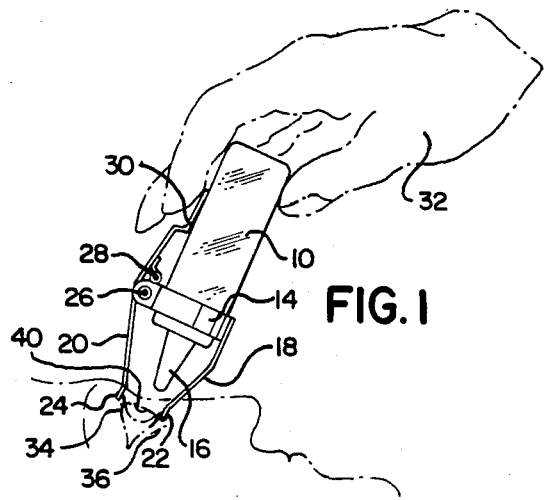
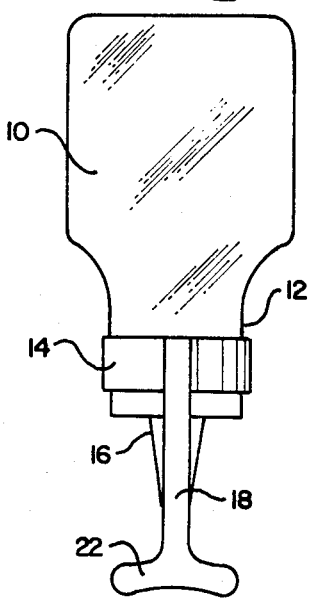
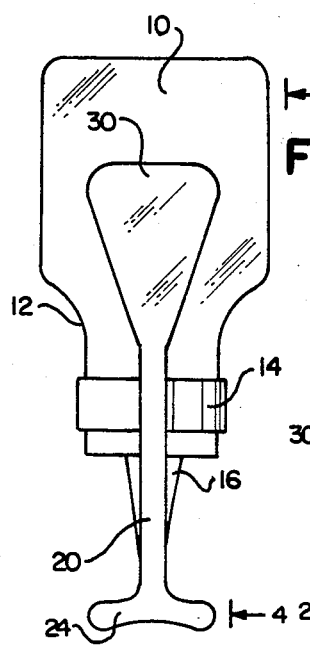
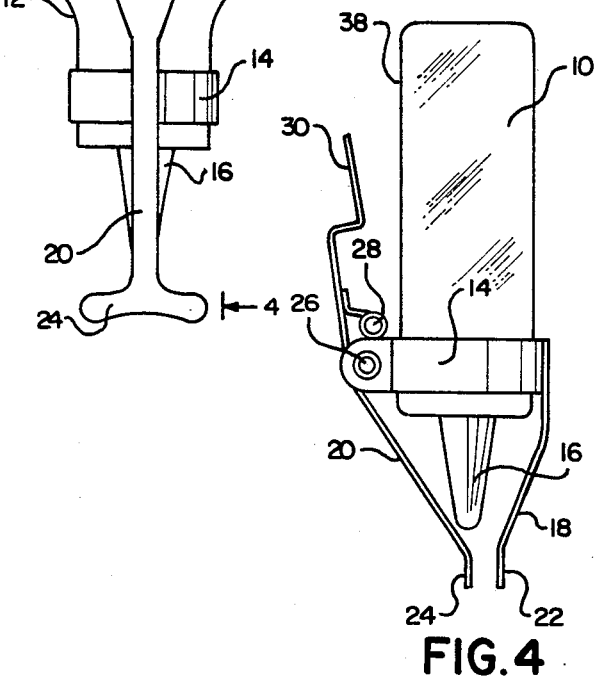
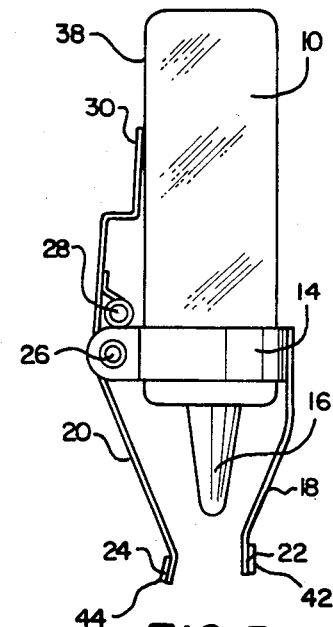

EYEDROP DISPENSER WITH EYELID OPENING MEANS

FIELD OF THE INVENTION

The invention relates generally to the field of eyedroppers and eyewash dispensers, and more particularly, is directed to an eyedrop dispenser to be used in the self-administration of drops to the users' eyes.

BACKGROUND OF THE INVENTION

The human eye is extremely sensitive to dust and other small foreign objects. When such materials inadvertently come into contact with the eyes, they usually quickly become quite irritated. One commonly accepted method of alleviating this condition is to apply a mild liquid medicant to the eyes, which medicant is usually referred to as an eyewash. In other instances, in the case of eye irritation, eye strain and the like, it is also the usual practice to apply liquid medicants, usually by employing an eyedropper.

At the present time, it is necessary when dropping medicine into one's own eyes, to hold the head back and then drop the liquid medicines into the eyes from a dropper or dispenser bottle which is supported solely by the user's hand. Such a means of self-administering drops to one's eyes has the disadvantage that it is difficult to hold the hand steady enough to always drop the medicine at just the right place. Frequently, the hand may move sufficiently, as the dropper bulb or the dispenser bottle is being squeezed, to cause the lower end of the dropper to move from a position in registry over the eye, so that when the droplet of medicine separates from the dispenser, it may drop onto the face area adjacent to the eye instead of directly into the eye where it is needed.

Additionally, another particularly annoying problem or difficulty arises when self-applying an eyewash or other liquid to the eyes. That is, it is usually difficult to maintain the eyelids in an open position during the application of the liquid medicant.

SUMMARY OF THE INVENTION

This invention relates generally to an eyedrop dispenser with eyelid opening means, and more particularly, relates to a liquid eyewash dispensing device comprising a container in combination with an eyelid opening assembly whereby the eyelids may be maintained in an open position when the liquid medicant is being applied to an eye.

In accordance with the teachings of the present invention, a usual eyedrop or eyewash dispensing container, such as a plastic squeeze-type bottle with a dispensing nozzle is employed. A collar is supported about the neck of the container to carry an eyelid opening assembly forwardly of the nozzle.

The eyelid opening assembly includes a pair of eyelid engaging fingers. One finger is preferably fixed in position and has no movement relative to the collar or to the container. The second finger is pivotally supported on the collar and includes a spring biased operating lever for eyelid opening purposes. This spring normally biases the movable finger toward the fixed finger so that upon pressing the operating lever, the movable finger will move away from the fixed finger, against the bias of the spring, to thus urge the eyelids apart for eyedrop or eyewash dispensing purposes.

It is therefore an object of the present invention to provide an improved eyedrop dispenser with eyelid opening means of the type set forth.

It is another object of the present invention to provide a novel eyedrop dispenser including an easily attachable and inexpensive eyelid opening assembly.

It is another object of the present invention to provide a novel eyedrop dispenser including a plastic squeeze bottle having a dispensing nozzle at one end thereof, a collar fitted about the neck of the bottle, the collar carrying a pair of cooperating fingers for eyelid opening purposes and lever means to move one finger relative to the other for separation of the eyelids during the eyedrop dispensing operation.

It is another object of the present invention to provide a novel eyedrop dispenser that is inexpensive in manufacture, simple in design and trouble free when in use.

Other objects and a fuller understanding of the invention will be had by referring to the following description and claims of a preferred embodiment thereof, taken in conjunction with the accompanying drawings, wherein like reference characters refer to similar parts throughout the several views and in which:

BRIEF DESCRIPTION OF THE DRAWINGS

FIG. 1 is a perspective view, on reduced scale, showing the eyedrop dispenser of the present invention in use.

FIG. 2 is a side elevational view of the eyedrop dispenser illustrating particularly the fixed finger.

FIG. 3 is a side elevational view of the opposite side of the dispenser illustrated in FIG. 2, showing particularly the movable finger.

FIG. 4 is an end elevational view of the eyedrop dispenser, looking from line 4—4 on FIG. 3.

FIG. 5 is a view similar to FIG. 4, showing the movable finger pivoted to the eyelid opening position.

DESCRIPTION OF THE PREFERRED EMBODIMENT OF THE INVENTION

Although specific terms are used in the following description for the sake of clarity, these terms are intended to refer only to the particular structure of the invention selected for illustration in the drawings, and are not intended to define or limit the scope of the invention.

Referring now to the drawings, there is illustrated in FIG. 1 an eyedrop dispenser with eyelid opening means in accordance with the present invention which includes generally a conventional plastic squeeze type bottle 10 of suitable configuration and composition to retain therein a quantity of liquid eye medication, for example, eyedrops. The bottle 10 is forwardly constricted to define a neck 12, which neck is conventionally configured to mount a dispensing nozzle 16 thereupon. The interconnection between the nozzle 16 and the bottle neck 12 is configured in the usual manner to facilitate loading the liquid eyedrops (not illustrated) into the hollow interior of the bottle 10 in a leakproof manner whereby the bottle can be readily carried about without unwanted leakage at the nozzle 16.

Still referring to FIG. 1, it will be seen that the liquid medicine contained within the bottle 10 can be easily dispensed through the nozzle 16 by squeezing the bottle 10. In the illustrated embodiment, the thumb and forefinger of the user's hand 32 can readily be employed to squeeze the sides of the bottle 10 sufficiently to expel the liquid medicine drop by drop through the tip of the nozzle 16.

Referring now to FIGS. 2 and 3, it will be seen that the eyelid opening means comprises the operating combination of a fixed finger 18 and a movable finger 20. A collar 14 is suitably secured about the bottle neck 16 in well known manner, for example, by employing a friction fit. The collar 14 has secured thereto the fixed finger 18 which extends forwardly of the nozzle 16 and terminates forwardly in a relatively flat eyelid contactor 22. Preferably, the collar 14 and the fixed finger 18 are fabricated of suitable relatively hard plastic of the type suitable to maintain the desired shape as illustrated and which exhibits sufficient rigidity to prevent ready deformation when in use. Preferably, the forward eyelid contactor 22 may be equipped with a protector 42 of foam plastic or other soft material of complementary shape to bear against the user's eyelid without causing undue discomfort or even injury.

The movable finger 20 is pivotal relative to the collar 14 and includes generally a central pivot 26, a rearward finger operator 30 and a forward, relatively flat eyelid contactor 24. A spring 28 continuously biases against the operator portion of the movable finger to continuously urge the movable finger contactor 24 toward the fixed finger eyelid contactor 22.

Preferably, the movable finger eyelid contactor 24 is similar in shape and construction to the fixed finger eyelid contactor 22 and also may be equipped with a suitable soft, foamlike protector 44 to prevent discomfort to the user when the eyedrop dispenser is intended to be used.

Referring now to FIGS. 4 and 5, it will be seen that the spring 28 normally biases the movable finger operator 30 away from the sidewalls of the bottle 10 whereby the movable finger rotates about its pivot 26 to urge the movable finger contactor 24 toward the fixed finger eyelid contactor 22. In the illustrated embodiment, the respective eyelid contactors 22,24 never touch, but are always separated by a space that is less than the distance between the eyelids of the user when the eyes are open. When the operator 30 is pressed by the fingers of the user's hand 32 to contact the sidewalls of the bottle 10, the movable finger 20 will pivot at 26 to separate the eyelid contactors 22,24 whereby the eyelids may be maintained in an open position when the eyedrops (not shown) are dispensed from the bottle 10 through the elongated nozzle 16.

In order to use the eyelid dispenser with eyelid opening means of the present invention, the device is grasped by the hand 32 of the user with the eyelid contactors 22,24 in their normally close or closed position as illustrated in FIG. 4. The eyelid contactors 22,24 can then be applied carefully and gently against the eyelids 34,36 of the user after the user has first tilted his head rearwardly so that the eye generally faces upwardly. See FIG. 1.

With the eyelid contactors 22,24 initially applied against the eyelids 34,36, the operator 30 can then be pressed by a finger of the user's hand 32 until the operator 30 contacts the sidewall 38 of the bottle 10. As illustrated in FIG. 1 and FIG. 5, by pressing the operator 30 against the bottle sidewall 38, the eyelid contactor 24 of the movable finger 30 will move away from the fixed finger contactor 22 to thereby spread the eyelids and to maintain the eyelids apart during the eyedrop or eyewash dispensing operation. With the eyelids 34,36 thus separated, the user can simply continue to squeeze the operator 30 against the container sidewalls 38 to thereby squeeze the bottle 10 and cause the liquid medicine to exit through the tip of the nozzle 16 for direct application upon the user's eye 40. It is noteworthy that the contactors 22,24 will remain associated with the user's eyelids 34,36 during the eyedrop dispensing operation and will prevent the eyelids from inadvertently closing to interfere with the application of the medicine.

Although the present invention has been described with reference to the particular embodiments herein set forth, it is understood that the present disclosure has been made only by way fo example and that numerous changes in the details of construction may be resorted to without departing from the spirit and scope of the invention. Thus, the scope of the invention should not be limited by the foregoing specification but rather only by the scope of the claims appended hereto.

What is claimed is:

1. In an eyedrop dispenser of the type including a bottle having a liquid dispensing nozzle, the combination of
   a collar secured about the bottle, the collar comprising a pivotal connection;
   a pair of elongated cooperating first and second fingers secured to the bottle,
      the first and second fingers terminating forwardly in respective first and second eyelid contactors,
      the first of the fingers being adapted for movement relative to the bottle about the pivotal connector to move the first eyelid contactor relative to the second eyelid contactor, the second finger being fixedly connected to the collar and having no movement relative to the bottle,
      the first and second eyelid contactors being positioned forwardly of the bottle dispensing nozzle;
   spring means to normally bias the first eyelid contactor toward the second eyelid contactor; and
   operator means to overcome the bias of the spring means to move the first eyelid contactor away from the second eyelid contactor,
      the operator means comprising a pivot connected to the pivotal connection of the collar and an operator integral with and extending from the first finger;
   whereby the eyelids of the user may be separated and eyedrops can be dispensed from the nozzle in a simultaneous manner when the operator is moved about the pivot and a portion of the operator is pressed into contact with the bottle.

2. The dispenser of claim 1 wherein the spring means is positioned at the pivotal connection, the spring means biasing between a portion of the collar and a portion of the operator.

3. The dispenser of claim 2 wherein the operator is bent intermediate its length to define an operating lever, the operating lever being the portion that is pressed into contact with the bottle.

* * * * *